United States Patent
Raybin et al.

(10) Patent No.: US 9,561,048 B2
(45) Date of Patent: Feb. 7, 2017

(54) EXPANDABLE ENDOSCOPIC HOODS AND RELATED METHODS OF USE

(71) Applicants: Samuel Raybin, Marlborough, MA (US); Ruth Cheng, Natick, MA (US); Paul Smith, Smithfield, RI (US); Naroun Suon, Lawrence, MA (US)

(72) Inventors: Samuel Raybin, Marlborough, MA (US); Ruth Cheng, Natick, MA (US); Paul Smith, Smithfield, RI (US); Naroun Suon, Lawrence, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 298 days.

(21) Appl. No.: 13/774,719

(22) Filed: Feb. 22, 2013

(65) Prior Publication Data

US 2013/0225934 A1 Aug. 29, 2013

Related U.S. Application Data

(60) Provisional application No. 61/602,372, filed on Feb. 23, 2012.

(51) Int. Cl.
| | |
|---|---|
| *A61B 17/32* | (2006.01) |
| *A61B 17/02* | (2006.01) |
| *A61B 17/3205* | (2006.01) |
| *A61B 17/00* | (2006.01) |

(52) U.S. Cl.
CPC ... *A61B 17/320016* (2013.01); *A61B 17/0218* (2013.01); *A61B 17/32056* (2013.01); *A61B 2017/00269* (2013.01); *A61B 2017/00867* (2013.01); *A61B 2017/320044* (2013.01)

(58) Field of Classification Search
CPC ............. A61B 1/32; A61B 1/005; A61B 1/00; A61B 1/00135; A61B 1/00137
USPC ....... 600/101, 104, 127, 562, 564, 566, 567; 606/45, 46, 170, 167
See application file for complete search history.

(56) References Cited

U.S. PATENT DOCUMENTS

| | | | |
|---|---|---|---|
| 5,337,754 A | 8/1994 | Heaven et al. | |
| 6,139,508 A | 10/2000 | Simpson et al. | |
| 2006/0235417 A1 | 10/2006 | Sala | |
| 2007/0135686 A1* | 6/2007 | Pruitt | A61B 17/0218 600/214 |
| 2008/0058590 A1* | 3/2008 | Saadat | A61B 1/00085 600/109 |

(Continued)

OTHER PUBLICATIONS

International Search Report for corresponding international application PCT/US2013/027439, mailed Nov. 6, 2013, 4 pages.

*Primary Examiner* — Ellen C Hammond
*Assistant Examiner* — Christina Negrellirodrigue
(74) *Attorney, Agent, or Firm* — Bookoff McAndrews, PLLC

(57) ABSTRACT

A medical device for tissue resection and related methods of use are disclosed. The device may include an elongate member having a proximal end and a distal end. The distal end of the elongate member may include a distal portion defining an end face and a cavity extending distally therefrom. The distal portion may further include multiple sections configured to transition between a first position and a second position different from the first position. The medical device may further include a mechanism configured to adjust a volume of the cavity by moving at least one of the multiple sections from the first position to the second position.

18 Claims, 7 Drawing Sheets

(56) References Cited

U.S. PATENT DOCUMENTS

| | | |
|---|---|---|
| 2008/0269557 A1 | 10/2008 | Marescaux et al. |
| 2009/0076498 A1* | 3/2009 | Saadat et al. .................. 606/41 |
| 2010/0274275 A1 | 10/2010 | Stammberger et al. |
| 2011/0060188 A1* | 3/2011 | Sharon .................. A61B 10/06 600/106 |
| 2011/0098531 A1 | 4/2011 | To |

* cited by examiner

EXPANDABLE ENDOSCOPIC HOODS AND RELATED METHODS OF USE

CROSS-REFERENCE TO RELATED APPLICATION

This application claims the benefits of priority under 35 U.S.C. §119 to U.S. Provisional Patent Application No. 61/602,372, filed Feb. 23, 2012, entitled EXPANDABLE ENDOSCOPIC HOODS AND RELATED METHODS OF USE, the entirety of which is incorporated herein by reference.

FIELD OF THE INVENTION

This disclosure relates generally to devices and methods for dissecting and resecting tissue. More particularly, embodiments of the disclosure relate to minimally invasive devices and methods for endoscopic mucosal resection, endoscopic submucosal dissection, and per-oral endoscopic myotomy (POEM).

BACKGROUND OF THE INVENTION

Organ walls are composed of several layers: the mucosa (the surface layer), the submucosa, the muscularis (muscle layer), and the serosa (connective tissue layer). In gastrointestinal, colonic, and esophageal cancer, e.g., small polyps or cancerous masses may form along the mucosa and often extend into the lumens of the organs. Conventionally, this condition is treated by cutting out a portion of the affected organ wall. This procedure, however, may cause discomfort to patients, and pose health risks. Recently, physicians have adopted a minimally invasive technique called endoscopic mucosal resection (EMR), and another called endoscopic submucosal dissection (ESD), which removes the cancerous or abnormal tissues (e.g., polyps), keeping the walls intact. EMR may also assist in removing any undesired tissue, even if such tissue is not abnormal or diseased. For purposes of this disclosure, the term "lesion" or "abnormality" includes, and will be used to refer to, these cancerous or abnormal tissues generally.

EMR and ESD are generally performed with an endoscope, which may be a long, narrow elongate member optionally equipped with a light, imaging device, and other instruments and defining a lumen extending from a proximal to a distal end of the elongate member. During ESD, the endoscope is passed down the throat or guided through the rectum to reach an undesired tissue, such as a polyp, in an affected organ. The distal end of the endoscope, typically equipped with a hood carrying dissecting tools such as a small wire loop, a band, or a knife is guided towards the undesired tissue. For EMR, the undesired tissue may be drawn into the hood. This may be achieved by applying suction through working channel extending along the lumen, or by retracting a retraction tool that is extendable from the endoscope. When the undesired tissue is sufficiently drawn into the hood, the dissecting tool may dissect portions of the tissue or resect target tissue from the organ wall. Subsequently, the excised tissue may be extracted for examination, biopsy, or disposal.

For ESD, the hood is typically used to create a working volume, applying tissue tension for endoscopic instruments, and preventing extraneous tissue and debris from interfering with the operator's visualization and operation.

Conventional endoscopic hoods may provide sufficient volume to operate on, e.g., small areas of target tissue (~smaller than 30 mm), but prove insufficient for dissecting, e.g., larger areas of target tissue (~larger than 30 mm). The volume offered by conventional hoods is not sufficient to effectively grasp and resect larger tissue area, such as, e.g., large lesions. As a result, certain large lesions may not be resected properly, forcing the operator to perform the procedure multiple times. Numerous attempts, along with increased operation time, increase the risk of damaging the submucosal wall and causing irreparable damage to the surrounding tissue.

Therefore, there exists a need for an improved ESD or resection hood that aids in grasping and/or dissecting tissue and resecting small and large areas of target tissue without damaging the surrounding tissue or muscle layers of the organ.

SUMMARY OF THE INVENTION

Embodiments of the present disclosure provide a device for resecting an undesired mass or otherwise unwanted tissue from a patient's body using a minimally invasive surgical method.

In accordance with an aspect of the present disclosure, a medical device may include an elongate member having a proximal end and a distal end. The distal end of the elongate member further includes a distal portion defining an end face and a cavity extending distally there from. The distal portion further including a plurality of sections configured to transition between a first position and a second position different than the first position. Further, a mechanism may be configured to adjust a volume of the cavity to, e.g., allow for resection of larger tissue volumes, by moving at least one of the plurality of sections from the first position to the second position. In other instances, the embodiments disclosed herein may be used to separate tissue layers along natural intersections. For example, the embodiments of FIGS. 3A-3B may be used for tunneling and separating the muscularis layer from the mucosal layer. The hood may be used as blunt plow-like device, or may be opened to force the layers apart. Further, the embodiments disclosed herein may be used to place tissue under tension to, e.g., assist in cutting the tissue.

In various embodiments, the device may include one or more of the following features: the distal portion may be removably coupled to elongate member; the plurality of sections may include two sections; the plurality of sections may include four sections; the cavity may include a distally-facing opening; at least one of the plurality of sections may be biased towards the first position; the elongate member may further include a plurality of channels extending between the proximal and distal ends; a tissue cutting device may be disposed in one of the plurality of channels; and at least one of the plurality of sections may include edges configured to cut through tissue. Further, the devices disclosed herein may be shaped (e.g., tapered or pointed) to aid in delivery through tissues or tight spaces. That is, the devices disclosed herein may include a leading nose to assist in delivery.

In accordance with another aspect of the invention, a medical device may include an elongate member having a proximal end, a distal end, and a lumen extending therebetween. The distal end may define an end face of the elongate member. The medical device further includes a hood having a proximal end and a distal end, such that the proximal end is configured to receive the distal end of the elongate member. Further, a distal portion of the hood includes a plurality of sections configured to transition between a closed state and an open state, the plurality of sections defining a cavity extending distally from the end face of the elongate member.

In various embodiments, the device may include one or more of the following features: the hood may include a flexible material and the plurality of sections may be formed by slits introduced in the flexible material; the plurality of sections may include four sections; wherein, when the plurality of sections are in the open state, the cavity may include a distally-facing opening; wherein, when the plurality of sections are in the closed state, the cavity does not include a distally-facing opening; and wherein transitioning the plurality of sections from the closed state to the open state increases a dimension of the cavity. Further, the hoods disclosed herein may include a lubricious material, coating, or surface geometry.

In accordance with yet another aspect of the invention, a medical device may include an elongate member having a proximal end, a distal end, and a lumen extending therebetween. The distal end defines an end face of the elongate member. The medical device further includes a hood including a proximal end and a distal end. A distal portion of the hood includes a plurality of sections configured to transition between a closed state and an open state. The plurality of sections may define a cavity extending distally from the end face of the elongate member. The device may further include a sheath including a proximal end, a distal end, and one or more channels extending therebetween. The sheath may be configured to slidably receive the hood within one of the channels. The hood may be configured to transition between the closed state while in the channel of the sheath and the open state while out of the channel.

In various embodiments, the device may include one or more of the following features: the plurality of sections may be made integrally with one another; the plurality of sections may be biased towards the open state; and a device configured to sever tissue.

Additional objects and advantages of the instant disclosure will be set forth in part in the description, which follows, and in part will be obvious from the description, or may be learned by practice of the present disclosure. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Figure 1:
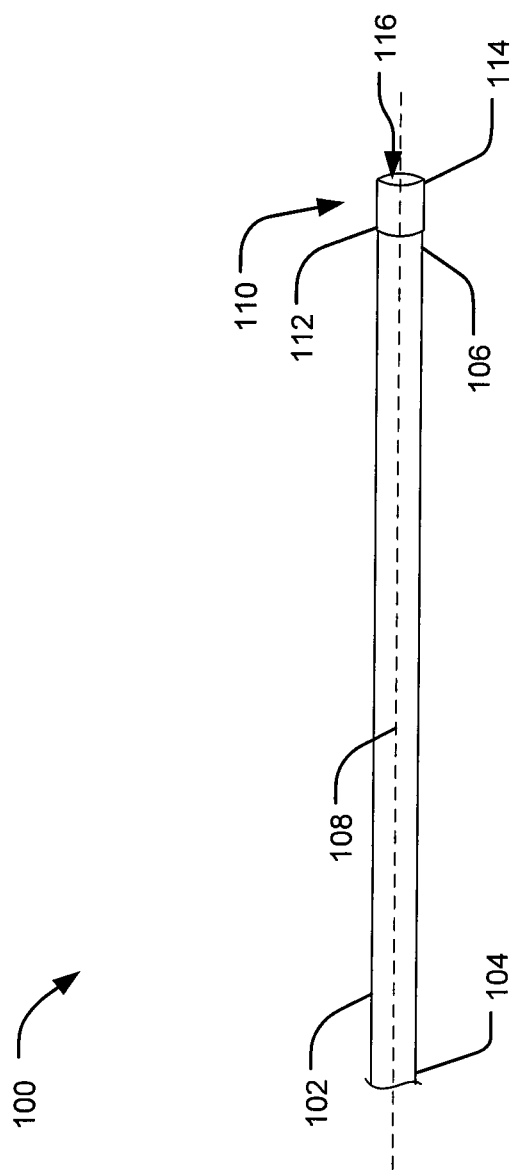
FIG. 1 is a side view of an exemplary endoscopic resection device, according to an embodiment of the present disclosure.

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to devices and methods for moving through tissues, manipulating tissues, making space (for procedures) within tissues, and dissecting or resecting undesired tissue (e.g., cancerous lesions and/or polyps) from within a patient's body. For example, the device may be used in a minimally invasive procedure to remove cancerous polyps or lesions from the mucosal walls of the colon, esophagus, stomach, duodenum, or any other suitable location. In fact, those of ordinary skill will readily recognize that the principles of the present disclosure may be used to remove target tissue from any location within a patient's body, regardless of whether the target tissue is abnormal or diseased. A physician may also wish to resect tissue to conduct a biopsy or other examination. It should be understood that the resection device may perform the functions of dissecting, transecting, resecting, retrieving, or another medical procedure, but for convenience, the term "resection device" will be used throughout this application.

For conducting such procedures, embodiments of the resection device described in this disclosure include an ESD, EMR, and/or POEM hood assembly coupled to a distal portion of any suitable elongate member or other introduction sheath, such as an endoscope, that is operable to create a working volume that is approximately the size of the tissue area targeted for removal. To this end, the hood may be expandable to increase its working volume according to the size of the targeted tissue area. The present disclosure illustrates various embodiments of an expandable hood, in accordance with the present disclosure. It will be understood, however, that these embodiments are not exhaustive and that many other configurations are conceivable and within the scope of the present disclosure.

In the following sections, embodiments of the present disclosure will be described using an exemplary body organ—the gastrointestinal tract. The embodiments of the resection device aim effectively to dissect and/or remove desired tissue, such as, e.g., lesion on an inner wall of the stomach, without damaging the underlying tissue layers. It will be understood that the stomach is merely exemplary, and that the device may be utilized in any other suitable organ, including the gastrointestinal tract, such as the colon, duodenum, esophagus, or any other organ where tissue removal may be desired. In addition, it will be understood that the principles of the present disclosure may be used to remove other objects such as, e.g., kidney or biliary stones, previously placed implants, or any other desired masses from within a patient's body.

Exemplary Embodiments

FIG. 1 is a side view of one embodiment of a resection device 100 of the present disclosure for dissecting and/or resecting polyps, lesions, or other undesired tissue from the interior bodily walls of a patient. Resection device 100 includes an elongate member 102 having a proximal end 104, a distal end 106, and a lumen 108 extending between proximal and distal ends 104, 106. Proximal end 104 may be coupled to a handle (not shown), while distal end 106 may be permanently or removably coupled to a hood 110. In some embodiments, hood 110 may be made integrally with distal end 106.

Elongate member 102 may be any flexible or rigid member adapted to be inserted into a patient. Further, elongate member 102 may be flexible in certain portions and rigid in others. For example, the elongate member's distal end 106 may be flexible or steerable, allowing the member to traverse circuitous cavities or lumens, while the rest of the member may be rigid to allow the elongate member 102 to be inserted into a body cavity.

In the illustrated device, elongate member 102 has a generally circular cross-section, with a generally circular hollow interior lumen 108, although not so limited in various embodiments. Indeed, elongate member 102 and lumen may have any suitable cross-section geometries, including, e.g., rectangular and/or ovular. Further, elongate member 102 may have a uniform diameter or may be tapered at the distal end 106 to facilitate insertion into a patient's body. Depending upon the particular implementation and intended use, the length and configuration of elongate member 102 may vary.

Lumen 108 may include one or more channels (not shown). Through these channels, an operator may introduce one or more medical devices to extend out of the distal end 106. For example, during a resectomy, the operator may introduce a suction device into one channel and a snare loop into another. Additionally, from time to time, during a procedure, the operator may introduce a light source, a camera, an injector, or a morcellator into one or more of the other channels. Because different implements may need to be inserted into the elongate member 102, the dimensions of its channels may vary. Some channels may have a larger diameter, while others may have a smaller diameter. Further, some channels may include permanently fixed medical devices, such as light sources or imaging devices, while other channels may allow temporary insertion and removal of medical devices, as the operator desires.

The elongate member 102 may be coated with lubricious materials and antibacterial agents to ease insertion into tight cavities and prevent infections, respectively. In addition, elongate member 102 may comprise lubricious materials or surface designs. Further, portions of the elongate member 102 may include radiopaque materials to visualize the position of elongate member 102 within a patient's body. Elongated member 102 described here may be any well-known endoscopic device used for colonoscopy, resectoscopy, cholangioscopy, or mucosal resection, and thus, this device will not be discussed in detail in the remainder of the disclosure.

Hood 110 may be a generally tubular elongated member configured to be secured to the elongated member's distal end 106. In the depicted embodiment, for example, hood 110 may include a proximal portion configured to fit over distal end 106. Alternatively, hood 110 may be configured to fit into and extend from a lumen of elongated member 102. The hood 110 has a proximal end 112, a distal end 114, and a lumen 116 extending from the hood's proximal end 112 to the hood's distal end 114. The hood may further include a mechanism allowing it to transition between two states: a first state, in which the hood is closed or has a reduced diameter and an expanded state, in which at least a distal portion of the hood is expanded radially. The diameter of the hood in its first state may, for instance, be similar to that of the elongate member 102. The expansion mechanism may include pull wires, elongate tubes, springs, levers, pulleys, or other mechanisms for reconfiguring the hood to the expanded state.

Hood 110 may be temporarily or permanently attached to the elongate member's distal end 106. By configuring the hood to complementarily engage with the distal end of a conventional endoscope or catheter, the hood can be used with existing endoscopes and catheters. A permanently attached hood ensures that hood 110 does not inadvertently separate from the elongate member's distal end 106 during a procedure. On the other hand, however, a removably coupled hood may allow for utilizing hoods of differing sizes. Based on the desired application, hoods may be manufactured either permanently attached to the distal end of elongate member 102 or with attachment means to temporarily attach the hoods 110 to elongate members 102 having complementary attachment means.

For temporary attachment, the proximal portion of the hood may include a substantially open attachment section, e.g., cylindrical, defining a recess for receiving a distal end of elongate member 102. The recess may include threading, projections, grooves, or any other temporary attachment means for attaching the hood to complementary structures on the elongate member. Thus, temporary attachments may, for instance, be defined by a screw-fit, Luer taper, snap-fit, or compression fit arrangement. In some embodiments, the attachment section may be adjustable, allowing operators to connect elongate members of varying configurations or sizes to the hood. For instance, the attachment section may be formed of a flexible material, such as elastic, or rubber, which may expand radially to allow the hood to fit over a range of elongate members with diameters greater than that of the hood's attachment section. It will be understood that the attachment section can be made from different materials and be configured differently to provide for adjustability without departing from the scope of the present disclosure. Furthermore, mechanisms for holding the attachment section to the endoscope may be used, including, e.g., hose clamps, wrapped filaments, clips, etc.

Permanent attachment may include welding, gluing, soldering, or other forms of attachment, or the hood 110 may be integrally formed with elongate member 102. It will be appreciated that other forms of temporary or permanent attachment may be adopted without departing from the scope of the present disclosure. In some embodiments, hood 110 may be integral with a sheath which fits along a portion of the endoscope from the distal end and proximally. In further embodiments, this sheath may extend substantially the entire length of the endoscope.

Hood 110 may be formed of any suitable biocompatible material, such as polyurethane, plastics, polymers, and metals including shape memory or superelastic materials for instance, Nitinol.

The hood 110 may also be coated with antibacterial and/or lubricious agents that prevent bacterial infections and/or allow the hood to easily pass through the lumens and cavities within a patient's body with minimal or no abrasion or bruising to surrounding tissue. Hood 110 may also comprise a lubricious material or surface, and/or surface designs that facilitate ease of insertion.

In the following sections, with reference to FIGS. 2-7, various exemplary embodiments of an expandable hood are described.

Figure 2A:
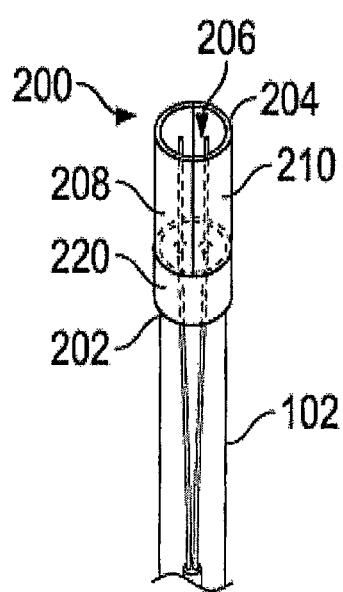
FIGS. 2A and 2B are perspective distal end views of an exemplary endoscopic hood in closed and expanded states, respectively, according to an embodiment of the present disclosure.
Figure 2B:
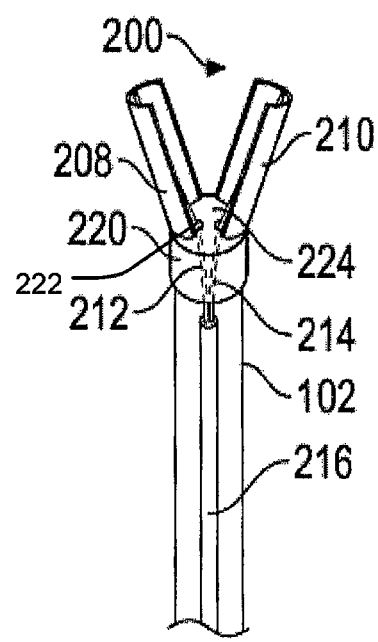

FIGS. 2A-2B is a perspective distal end views of an exemplary endoscopic hood 200 according to an embodiment of the present disclosure. More particularly, FIG. 2A illustrates hood 200 in a closed state and FIG. 2B illustrates the hood 200 in an open or expanded state. Here, as previously described, hood 200 includes a substantially tubular structure extending from a proximal end 202 to a distal end 204, and defines a lumen 206 extending from a proximal end 202 to a distal end 204. In the closed position, lumen 206 may define a working volume of the hood 200. Hood 200 in this embodiment takes the form of a hollow cylinder bisected into two substantially equal semi-cylindrical sections 208, 210 along a longitudinal axis. In some embodiments, the bisection is off-center, creating one section which is longer than the other. One advantage of such an embodiment may be to create a smaller leading distal tip on the hood. In the closed state, the two sections 208, 210 abut each other to form a circular distal opening, as shown in FIG. 2A. In the expanded state, the two sections 208, 210 may expand to increase the effective working volume of hood 200. In some embodiments, only one of sections 208, 210 may move relative to the other of sections 208, 210.

A portion, e.g., the proximal or distal ends, of each section 208, 210 maybe coupled to pull wires 212, 214. Although the depicted embodiments illustrate two pull wires 212, 214, some embodiments may include more or less (e.g., only one pull wire) pull wires. Further, a proximal portion of each of the two sections 208, 210 may be connected by means of hinges to a cylindrical attachment section 220, which connects the hood to the distal end of the elongate member 102. The hinge(s) may be a living hinge if each section is connected to the other toward a proximal end of hood 200. In another embodiment the sections 208, 210 may be coupled directly to the elongate member 102. The pull wires 212, 214 extend down the lumen of the elongate member 102 and are configured to be operable by a user at the proximal end of the elongate member 102 to move the sections 208, 210 between a closed state and an open state. In some embodiments, each of sections 208, 210 of hood 200 may be controlled independently. That is, each of sections 208, 210 may open or close independent of the other.

Depending on the points of attachment of the pull wires 212, 214 to the sections 208, 210, a tensile force on the wires will either close or open (expand) the hood. The pull wires 212, 214 may be sufficiently rigid to allow a compressive force to be transmitted to the sections 208, 210 to open or close the hood. Furthermore, the sections 208, 210 may be spring loaded or otherwise biased to remain in a normally open or normally closed position such that tensile force on the pull wires 212, 214 serves to close or open the hood against the natural bias. In other embodiments, an elastic band, e.g., may wrap around a portion of hood 200 to bias it to the closed position. In the embodiment of FIGS. 2A-2B, the pull wires 212, 214 are connected to points 222, 224, respectively. Thus, in order to keep the hood in the closed state (FIG. 2A), the pull wires are pulled at their proximal ends. In order to allow the hood to adopt its expanded configuration, the tensile force applied to the wires is released, allowing the sections 208, 210 to swing open.

The pull wires 212, 214 may be slidably mounted in a sheath 216, or two separate sheaths (not shown). Sheath 216, in one embodiment, is secured to the outer surface of elongate member 102 and extends from proximal end 202 of the hood 200 to the proximal end of elongate member 102. Any known securing means, such as retaining bands, clips, or fasteners, may be utilized to ensure that sheath 216 does not separate from the elongate member during operation. Alternatively, the sheath 216 may be present within the lumen of elongate member 102.

In other embodiments, pull wires 212, 214 may be mounted to run through one of the working channels of the elongate member 102 from the distal end to the proximal end of the elongate member 102, or one or more wire-supporting channels for supporting the pull wires may be formed into the walls of the elongate member 102. In yet another embodiment, sheath 216 may simply be secured to an inner wall of the elongate member using any known securing mechanism. It will be understood that other embodiments may be contemplated regarding the placement of pull wires relative to the elongate member 102, and none of these embodiments are outside the scope of the present disclosure.

In the embodiment shown in FIGS. 2A-2B, hood 200 may be substantially cylindrical in the closed state, having a circular distal opening. In other embodiments, however, the hood's shape may vary considerably. For example, the hood may have a conical, semi-elliptical, semi-circular, or pyramidal shape without departing from the scope of the present disclosure. In addition, a distal portion of hood 200 may include a raised portion, such as, e.g., a lip to allow better contact during vacuum application. The lip may include any suitable configuration and may be softer and/or wider than the remainder of hood 200.

Furthermore, in some embodiments, a proximal end portion of hood 200 may be hinged to allow the proximal end of the hood 200 to expand along with the distal end. For example, if a scissor arrangement of links is provided as a proximal hinge, the proximal end of the hood 200 may expand wider than the distal end.

Figure 3A:
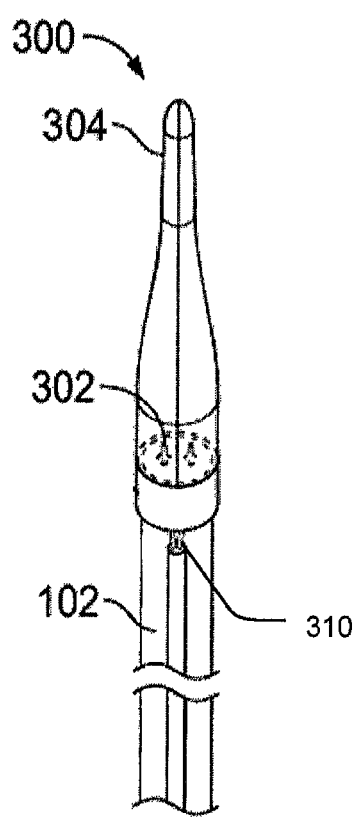
FIGS. 3A and 3B are perspective distal end views of an endoscopic hood in closed and expanded states, respectively, according to another embodiment of the present disclosure.
Figure 3B:
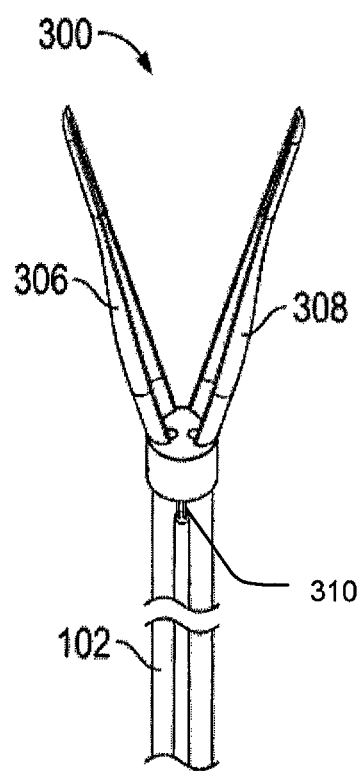

FIGS. 3A-3B depict end views of another exemplary hood 300, with FIG. 3A showing the hood 300 in a closed position and FIG. 3B showing hood 300 in an open or expanded position. Hood 300 extends from a proximal end 302 to a distal end 304, and may include one or more features of the other hood embodiments described herein, including those specifically described above with respect to FIGS. 2A-2B. Hood 300 may be shaped as a "duckbill," instead of a cylinder. Again, similar to the hood illustrated in FIGS. 2A-2B, the duckbill hood may be bisected longitudinally into two equal sections 306, 308. In this embodiment, the sections 306, 308 are pivotally connected directly to the distal end of elongate member 102, but could again be connected to an attachment section that secured the hood 300 to a distal end of elongate member 102.

Each section 306, 308 of the duckbill hood includes a proximal end 302 having diameter substantially similar to the elongate member's distal diameter. The distal ends of the sections 306, 308 taper such that when the two sections contact each other, there is no distal end opening. Outer surfaces of each section 306, 308 may include atraumatic configurations to eliminate the presence of any sharp edges or corners. Such a hood configuration may allow a user to grasp and securely retain therein, e.g., unwanted tissue or the like. In addition, when the duckbill hood 300 is in the closed position (see, e.g., FIG. 3A), the distal end 304 may be inserted in between two tissue portions and the hood may be opened to separate those tissue portions.

Sections 306, 308 transition from an expanded state to closed state using known mechanisms. In one embodiment, pull wires 310 extend from the proximal end of sections 306, 308 to a handle (not shown) operable by a user to move the sections 306, 308. Sections 306, 308 may assume their closed state by pulling the pull wires 310. By providing fairly rigid pull wires 310 that can support compressive forces, the pull wires 310 can also be used to open the hood 300 by pushing the pull wires.

In certain circumstances, the hood 300 may have to exert a radially outward force on the surrounding tissue in order to expand. For instance, in small cavities where large lesions are to be resected, hood 300 may not expand unless substantial radial force is exerted on the sections of the hood 300. Accordingly, the hood 300 may include some mechanism to exert this force. As discussed above, in some cases, the pull wires 310 may be rigid enough to provide the required force. In other embodiments, the hinged connection between the hood 300 and the elongate member 102 may include spring elements or certain groove and projection assemblies and pull wire connections that are configured to urge the sections of the hood 300 apart when a tensile force is exerted on the pull wires 310. In still further embodiments, sections 306, 308 may be biased either toward or away from one another.

For instance, in both the hood configurations illustrated in FIGS. 2A-2B and 3A-3B, the pull wires 310 may be attached to the distal ends of the hood sections instead of the proximal ends. To this end, the pull wires 310 may be coupled to the outer surface of the sections. Proximally pulling the pull wires 310 would then expand the hood 300 and distally pushing the pull wires 310 would urge the sections together to allow the hood 300 to assume its closed state. Other pull wire attachment locations may also be considered, such as centers, proximal portions, or distal portions of the sections, without departing from the scope of the present disclosure. In some embodiments, the distal end of the pull wires 310 may comprise a larger surface area than the body of the pull wires 310, e.g., by flattening the distal end. An increased surface area may increase the attachment strength of the pull wires 310 to the hood 300.

The duckbill configuration of hood 300 allows it to be wedged into small gaps of incisions so that the expanding action may dissect tissue in a blunt fashion along, e.g., natural tissue interfaces. As described previously other hood configurations may be also used.

Figure 4A:
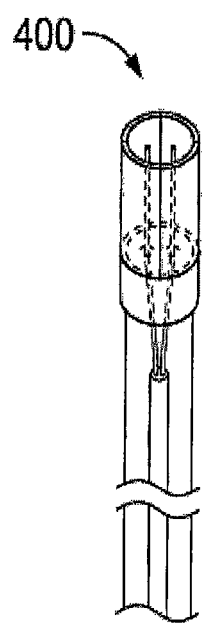
FIGS. 4A and 4B are perspective distal end views of an endoscopic hood in closed and expanded states, respectively, according to a further embodiment of the present disclosure.
Figure 4B:
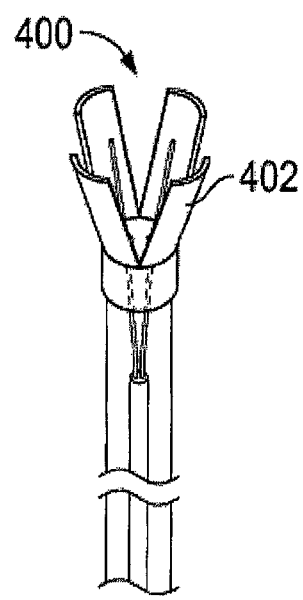

FIGS. 2A-2B and 3A-3B illustrate different configurations of hood embodiments, but in both of these configurations, the disclosed hood is essentially bisected into two sections. FIG. 4A is a perspective dimensional view of another embodiment of a hood 400 in the closed state and FIG. 4B shows the hood 400 in an expanded state. Here, the hood 400 includes more than two sections. In particular, this embodiment shows a hood comprising four sections, which come together to form a cylindrical shape member having a circular distal opening. In each of the embodiments described above, the hood is divided into two or more sections that assume a closed state and an expanded state. In the expanded state, the sections of the hood diverge from each other to increase the working volume of the hood. In the closed state, however, various sections of the hood come together to form a closed volume, which may either have a distal opening, shown in FIG. 2A, or the hood may be completely closed from its distal end, as shown in FIG. 3A.

Various alternatives of the hood 200 or 300 may be contemplated. It will be appreciated that the hood may include a greater or lesser number of sections without departing from the scope of the present disclosure. Four sections distribute the retraction force better than two sections and create a larger and more circular working volume. Even so, the present disclosure contemplates embodiments having two, three, or more sections. As in the embodiments discussed with respect to FIGS. 3A-3B and 4A-4B, the pull wires in this embodiment are coupled to the proximal ends of the sections but could again be attached to the distal ends of the sections or any portion along the length of the sections. Further, the illustrated embodiment has a cylindrical shape. Other shapes may however be implemented using more than two sections. For example, the duckbill hood may include four sections. Additionally, the plurality of sections may be connected by a flexible membrane (not shown) to allow for suction to the chamber when in the open position.

Figure 5A:
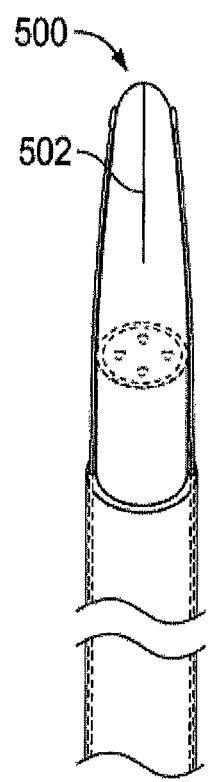
FIGS. 5A and 5B are perspective distal end views of an endoscopic hood in closed and expanded states, respectively, according to another embodiment of the present disclosure.
Figure 5B:
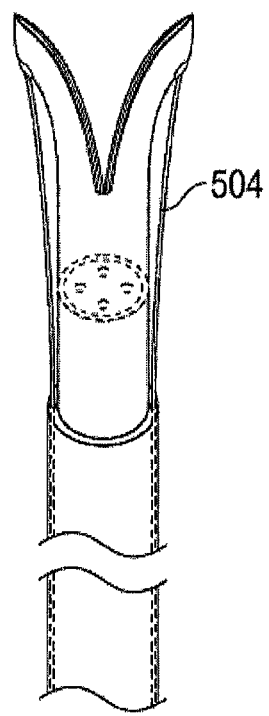

FIGS. 5A-5B are perspective views of yet another embodiment of a hood 500. FIG. 5A shows the hood 500 in a closed state and FIG. 5B shows the hood 500 in an open or expanded state. Here, instead of hinged sections, the hood 500 is made of a flexible material. A slit 502 is introduced in a distal portion of hood 500. As shown, for example, slit 502 may extend proximally from a distal end of hood 500 to a location distal of the proximal end of hood 500. Pull wires 504, attached to the outside distal portion of the hood 500 the elongate member exert a force on the distal end of the hood when pulled at the proximal end of the elongate member, thereby widening the slit 502 and expanding hood 500. In the closed state, however, the slit 502 is narrowed such that hood 500 remains completely closed from its distal end with no distal opening, as shown in FIG. 5A.

The hood 500 may be made of any suitable, substantially flexible material such as a plastic, polymer, elastomer, etc. Further, edges of the distal end of hood 500 may be sharpened or include cautery capabilities for tissue resection.

While the embodiment shown in FIG. 5 includes only one slit 502, more silts may be introduced in the distal end of the hood. It will be understood that the number of pull wires attached to hood 500 will vary based on the number of slits. For example, in case of one slit, two pull wires may be provided, while for two slits, four pull wires are preferably provided.

Further, the shape of hood may vary based on the desired application. In some cases, the hood may have a hollow cylindrical configuration, while in others, the hood may have a substantially dome shaped, duckbill shaped, conical, pyramidal, elliptical, or other shaped distal portion without departing from the scope of the present disclosure. In addition, the pull wires in the configuration of FIG. 5 may be attached to the inner distal surfaces of the hood. Distally pushing the pull wires, in such a scenario may expand the hood, increasing its volume.

Figures 6A, 6B, 6C:
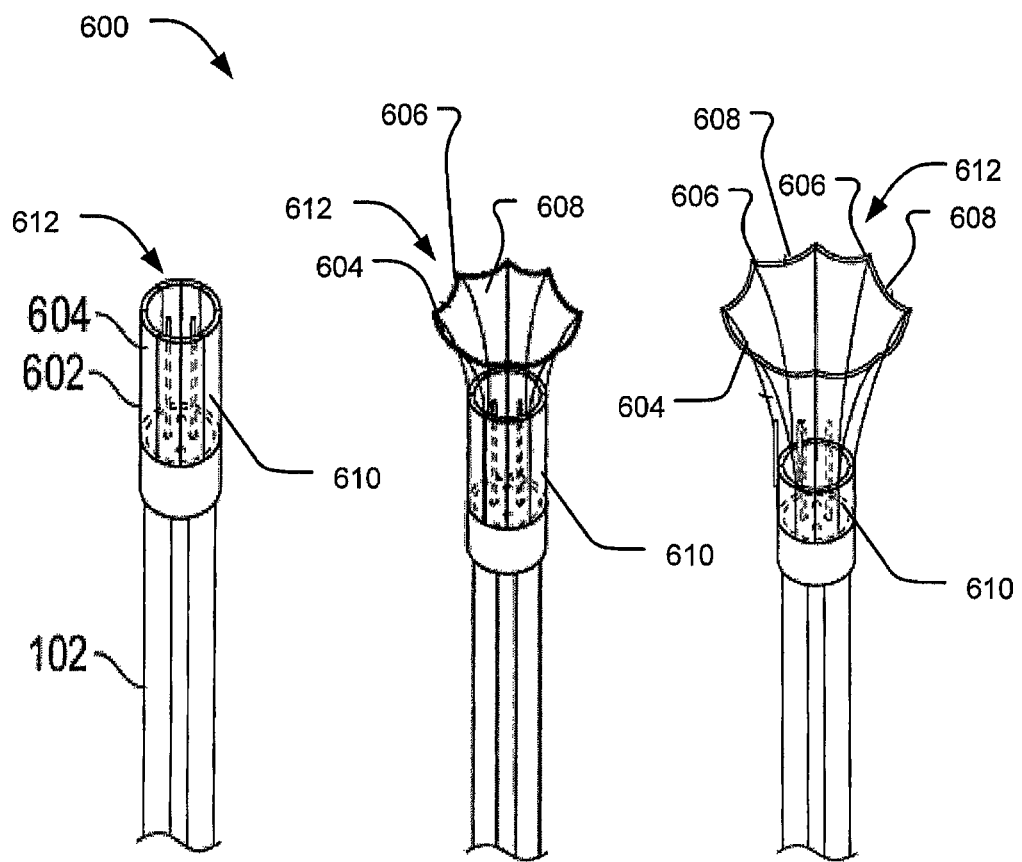
FIGS. 6A, 6B, and 6C are perspective distal end views of an endoscopic hood in different states of expansion, according to an even further embodiment of the present disclosure.

FIGS. 6A-6C are perspective views showing three positions of yet another embodiment of a hood of the present disclosure. As noted above, any embodiment disclosed herein may include one or more features described in connection with any of the other embodiments described herein. In the first position (FIG. 6A), hood 600 is in the closed state; in the second position (FIG. 6B), hood 600 is partially expanded; and in the third position (FIG. 6C), hood 600 is in an expanded state. Hood 600 includes a sheath 602, and an expandable hood portion 604 slidably mounted within a lumen 610 defined by the sheath 602. In the closed position, lumen 610 may define a working volume of the hood 600. Hood 600 takes the form of a hollow cylinder having expandable hood portion 604, which is divided into substantially equal sections along a longitudinal axis. In the closed state, the sections of hood portion 604 abut each other to form a closed cylinder having a circular distal opening, as shown in FIG. 6A. In the expanded state, however, the sections of hood portion 604 may expand to increase the effective working volume of hood 600.

In the embodiment shown, the sheath 602 extends over a distal portion 106 of the elongate member 102. In another embodiment (not shown), the sheath 602 may run along the entire outer surface of the elongate member 102. In yet another embodiment (not shown), sheath 602 may run along a portion or the entire length of the elongate member's inner surface.

Sheath 602 may be any flexible or rigid member adapted to include expandable hood portion 604 at its distal end. Further, sheath 602 may be flexible in certain portions and rigid in others. For example, the sheath's distal end may be flexible or steerable, allowing the hood 600 to traverse circuitous cavities or lumens.

In the illustrated device, sheath 602 has a generally circular cross-section, with a generally circular hollow interior lumen 610. Depending upon the particular implementation and intended use, the length and configuration of sheath 602 may vary.

Lumen 610 may include one or more channels (not shown). Through these channels, an operator may introduce one or more medical devices to extend out of the distal end 612. For example, the hood 600 may extend from one channel and other medical tools required for resection, visualization, may be introduced through other channels of the lumen 610.

The sheath 602 may be coated with lubricious materials and antibacterial agents to ease insertion into tight cavities and prevent infections, respectively. Further, portions of the sheath 602 may include radiopaque materials to visualize the position of sheath 602 within a patient's body. Sheath 602 described here may be any well-known endoscopic device used for colonoscopy, resectoscopy, cholangioscopy, or mucosal resection, and thus, this device will not be discussed in detail in the remainder of the disclosure.

In the embodiment of FIGS. 6A-6C, the expandable hood portion 604 is moveable between a closed state, within the sheath 602 and an open or expanded state in which it extends from the distal end of sheath 602. The expandable hood portion 604 includes urging means that urge the expandable hood portion 604 to expand outwardly in funnel-like fashion when not constrained by the sheath 602. In this embodiment, the urging means comprises multiple, substantially equidistant pull wires 606 encased in a flexible membrane 608. The illustrated embodiment includes six wires, but a greater or lesser number of wires may be used without departing from the scope of the present disclosure. Pull wires 606 may run along the length of elongate member 102, from its proximal end to its distal end, or the pull wires 606 may extend only along a distal portion of the elongate member 102. In one embodiment, pull wires 606 extend up to the proximal end of the sheath 602. In some instances, one or more of pull wires 606 may loop back on themselves to create yet another different profile. It should be understood that other expansion mechanisms, including springs, inflation balloon, etc., may also be employed. Further, a distal end portion of hood 600 may be reinforced with a ring to create a substantially smooth circular edge.

The distal portions of the wires in this embodiment are curved radially outwardly to create the outward urging force so that in the expanded state (FIG. 6C), when the expandable hood portion extends out of the distal end of the sheath 602, the expandable hood portion 604 spreads out to increase the working area of the hood 600. The entire lengths of the wires or the distal portions of pull wires 606 may be formed of shape memory materials such that in the normal state the distal portion of pull wires 606 curve outwardly from the central axis. When force is applied on the distal portions of pull wires 606, they may curve inward such that they are parallel to the central axis of the elongated member.

In operation, the expandable hood portion 604 remains within the sheath 602 when in the closed state. The sheath exerts a force on the wires maintaining them substantially straight within the sheath. An actuation mechanism, present at the proximal end of the elongate member 102, for instance as part of a handle, allows an operator to urge expandable hood portion 604 out of sheath 602 when the distal end 106 of the elongate member 102 is at the desired location within a patient's body. When expandable hood portion 604 extends beyond sheath 602, the sheath no longer exerts a force on the expandable hood portion, allowing the hood portion to curve outwardly.

In an alternate embodiment, the hood portions 604 may be self-expandable. The hood portion 604 may be disposed in a collapsed state within lumen defined by sheath 602. When appropriately positioned, sheath 602 may be pulled proximally allowing the hood 600 to extend distally from the sheath 602. As the hood 600 extends from the distal end of the sheath 604, the hood portions 604 expand into a pre-formed shape. In such embodiments, hood 600 may be formed of any suitable superelastic materials or shape memory material such as Nitinol.

Figure 7:
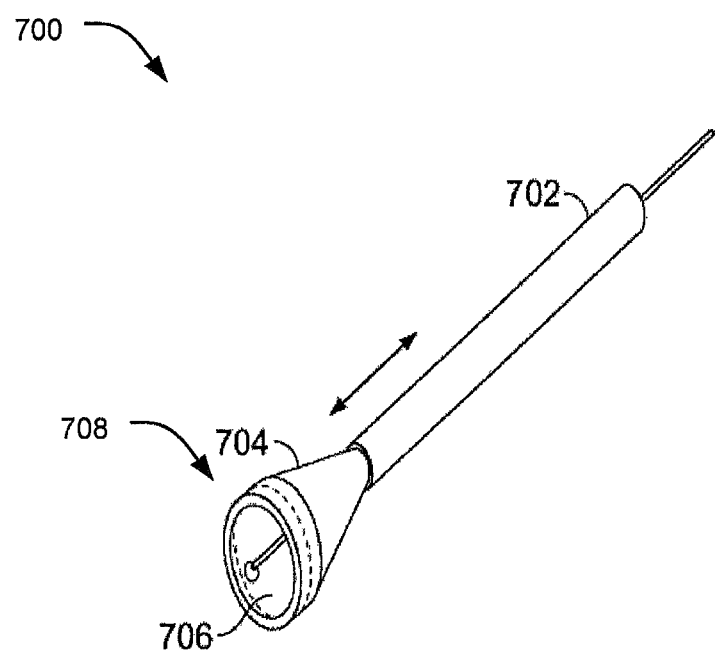
FIG. 7 is a perspective distal end view of yet another endoscopic hood, according to an embodiment of the present disclosure.

FIG. 7 is a perspective view of yet another embodiment of a hood. As noted above, any of the embodiments described herein may include one or more features of any of the other embodiments described herein. In this embodiment, hood 700 takes the form of a hollow cylinder, including an outer sheath 702 and an inner sheath 704. The inner sheath 704 is moveable between two positions—closed position (inside outer sheath 702), and expanded position (extending out of the distal end of outer sheath 702).

The inner sheath 704 may be formed of a self-expanding material, that when free of the force applied by outer sheath 702, expands into a distally flaring funnel. Any known self-expanding material may be utilized to form the inner sheath. For example, many flexible plastic materials having a memory will return to their natural relaxed state when constraining forces are removed. Thus, by forming such plastics material into a funnel shape, an inner expanding sheath can be provided that is constrained in its first position by the surrounding outer sheath 702 but will assume its funnel shape when extended from the outer sheath 702.

In another embodiment, inner sheath 704 may not be formed of a self-expanding member. In this case, the distal end 708 of inner sheath 704 may be selectively expanded by any suitable means. Suitable expansion mechanism may include, for example, springs, inflation balloon, etc. Alternatively, funnel may be removably coupled directly to the inner sheath 704. Funnel attachment means would be understood by a person of ordinary skill in the art.

One such means may be a cutting device, such as, e.g., a wire loop. In some embodiments, the cutting device may include cautery capabilities. Accordingly, the distal end of inner sheath 704 may include a circumferential channel 706, which may be connected to the elongate member's lumen through a small lumen (not shown) in the inner sheath 704. The cutting device may be inserted into channel 706 through the small lumen. By distally urging the cutting loop into circumferential channel 706, and by controlling the length of the cutting loop introduced into the channel 706, the distal diameter of inner sheath 704 may be varied. Thus, inner sheath 704 may be formed of a flexible member that is expandable when exposed to a force and contracts back to its original size once the expanding force is removed. In order to exert enough force to expand the inner sheath 704, the cutting loop should have certain rigidity. The required rigidity depends on the flexibility of inner sheath 704 and therefore, during manufacture, designers may consider the flexibility of inner sheath 704 and the rigidity of the cutting loop to design an effective expandable hood 700.

In the embodiments described with reference to FIGS. 2-7, any suitable material may be used to form the hood. For instance, rigid or semi-rigid materials such as metals (including shape-memory materials such as Nitinol), polymers, resins, super elastic materials, or plastics may be used. The hoods may also be optically transparent or translucent, allowing physicians to visualize the tissue being resected. Further, a biocompatible material that does not irritate the body lumens may be applied as a coating over the outer surfaces of the hoods.

Further, in all the embodiments described above, the hood is moveable between two states—closed and expanded. An actuation mechanism may be employed in all of the above embodiments to change the state of the hood. For example, the pull wires (in FIG. 6) may be coupled to an actuation mechanism on a handle. This mechanism may be a simple mechanical design such as a slider or a roller attached to the proximal ends of the pull wires. By moving the slider proximally or rotating the roller clockwise, the hood may be placed in the closed state, and by moving the slider distally or rotating the roller anti-clockwise, the hood may be placed in the expanded state. It will be understood that these mechanical mechanisms are merely illustrative and that other mechanical actuation mechanisms may instead be employed to actuate the hood.

In other embodiments, the actuation mechanism may be electronic or electromechanical, such as a digital touch pad, switch, or button. These and other actuation mechanisms are relatively well known in the art and will not be described any further in this disclosure. It will, however, be understood that any of these mechanisms may be employed to move the hood between its closed and its expanded state, without departing from the scope of the present disclosure.

By actuating the hood in its expanded state, encroaching tissue at the treatment site may be retracted providing more space for the operator to visualize and operate on the target tissue. Moreover, once the target tissue is dissected or resected, by placing the hood in its closed state, the dissected tissue may be captured in the hood and extracted with the endoscopic device when the device is retracted. By using the hood itself to behave as a grasper or a tissue capturing device, the need for a separate grasper or capturing tool may be eliminated. In such embodiments, the inner edges of the sections of the hood may include ridges, teeth, or other suitable geometric configurations to aid in tissue grasping and/or retraction. In minimally invasive and endoscopic procedures, where space is generally a constraint and time to exchange tools within the endoscope is a prime parameter in determining operating expense, utilizing the hood itself to grasp and retract tissue may be useful. In some embodiments, the dissected tissue may be extracted into the endoscopic device by suction mechanism.

The following section sets out an exemplary method for resecting lesions, polyps, or any other tissue from a patient's body. A typical location for a resection of this sort is the stomach, and that location will be discussed here. As will be understood by those in the art, other patient locations would be equally suitable. Either a percutaneous incision is made to access the gastrointestinal tract, or the resection device 100 may be inserted through a natural opening, such as the mouth.

Once inserted, the resection device 100 may be advanced to a location proximate the targeted tissue, e.g., a lesion located above the muscularis layer. During placement, a device with a hood embodiment disclosed herein, such as, e.g., hood 110, is maintained in the closed state such that it can pass through the small cavities within a patient's body without causing undue trauma. A steering mechanism may be incorporated in the resection device 100 (with controls in the handle) to guide and urge the device within a body cavity. A light source and a camera (not shown) may be inserted in the elongate member's lumen 108 to direct the device 100 within the stomach, and to identify target tissue, e.g., lesions. Various identification techniques may be employed. For example, a biomarker or dye may be applied around the gastrointestinal tract. Cancerous lesions, e.g., emit a different wavelength when light falls on them, allowing operators to easily detect them.

Once at the desired location, the hood 110 may be translated into its expanded state to push encroaching tissue away from the targeted tissue and increase the working volume of hood 110. The degree of expansion may be fixed, but in other cases, the degree of expansion may be configurable based on the size of the lesion. An actuation mechanism, present on the handle or a proximal portion of the elongate member, may be used to expand the hood and maintain it in the expanded state until the operation is complete or until such time as decided by the operator.

A grasper or suction may be provided through hood 110 to acquire the targeted tissue. Subsequently, the suction device may be powered off or removed, and a telescope or microscope (not shown) may be introduced into the elongated member 102, along with a light source (not shown), allowing a physician to closely examine the target tissue, and to determine whether the target tissue requires resection. Various other known techniques may be employed for this determination, without departing from the scope of the present disclosure.

Next, a resecting device, e.g., a cautery knife, snare loop, blade, ligating band or any other such tool, with or without energization, such as RF energy, may be introduced through hood 110 to sever the targeted tissue. Alternatively, the edges of the hood's distal opening may include resecting elements to cut tissue as the hood "closes" on the tissue.

Once the lesion is resected, device 100 may carry out any number of procedures to excise the resected matter. For example, resection device 100 may extract the lesion or morcellate it and then extract it. For extraction, hood 110 may simply be retracted to its closed state. While closing the hood 110 may grasp or capture the dissected tissue. Alternatively, a grasping or capturing device may be introduced into the hood 110 to extract the dissected tissue. In one embodiment, the lesion may be extracted with the help of suction force applied at proximal end 104 of resection device 100. In another embodiment, a basket, grasper, or pincers may be used.

Embodiments of the present disclosure may be used in any medical or non-medical procedure, including any medical procedure where appropriate resection of an undesired body tissue is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with the true scope and spirit of the present disclosure being defined by the following claims.

What is claimed is:

1. A medical device, comprising:
an elongate member having a proximal end and a distal end, wherein the distal end of the elongate member includes a distal portion defining an end face and a cavity extending distally therefrom, wherein the distal portion further includes a plurality of sections configured to transition between a first position and a second position different than the first position, and the plurality of sections are in contact in the first position and, wherein, when the plurality of sections are in the first position, a distal end of the cavity is closed, and wherein each of the plurality of sections includes a pair of edges each extending from a proximal end to a distal end of the corresponding section, and wherein, in the second position, adjacent edges of adjacent sections of the plurality of sections are unconnected by material to define an opening between the adjacent edges such that a circumferential space between the adjacent edges are free of material; and
a mechanism configured to adjust a volume of the cavity by moving at least one of the plurality of sections from the first position to the second position.

2. The medical device of claim 1, wherein the distal portion is removably coupled to the elongate member.

3. The medical device of claim 1, wherein the plurality of sections consists of two sections.

4. The medical device of claim 1, wherein the plurality of sections includes four sections.

5. The medical device of claim 1, wherein the cavity includes a distally-facing opening.

6. The medical device of claim 1, wherein at least one of the plurality of sections is biased towards the first position.

7. The medical device of claim 1, wherein the elongate member further includes a plurality of channels extending between the proximal and distal ends.

8. The medical device of claim 7, further comprising a tissue cutting device disposed in one of the plurality of channels.

9. The medical device of claim 1, wherein at least one of the plurality of sections includes edges configured to cut through tissue.

10. The medical device of claim 1, wherein each of the plurality of sections includes a proximal portion, an intermediate portion, and a distal portion, wherein the proximal portion is wider than the distal portion, and the intermediate portion tapers from a proximal end to a distal end.

11. A medical device, comprising:
an elongate member having a proximal end, a distal end, and a lumen extending therebetween, wherein the distal end defines an end face of the elongate member;
and a hood including a proximal end and a distal end, wherein the proximal end of the hood is configured to receive the distal end of the elongate member, and wherein a distal portion of the hood includes a plurality of sections configured to transition between a closed state and an open state, each of the plurality of sections defining two longitudinally extending edges, the plurality of sections defining a cavity extending distally from the end face of the elongate member, wherein, when the plurality of sections are in the open state, the cavity includes a distally-facing opening and a side opening between each pair of adjacent longitudinally extending edges of adjacent ones of the plurality of sections, wherein a circumferential space between each pair of adjacent longitudinally extending edges is free of material, and when the plurality of sections are in the closed state, the cavity does not include the distally-facing opening, and, when the plurality of sections are in the closed state, a distal end of the cavity is closed.

12. The medical device of claim 11, wherein the plurality of sections includes four sections.

13. The medical device of claim 11, wherein transitioning the plurality of sections from the closed state to the open state increases a dimension of the cavity.

14. The medical device of claim 11, wherein each of the plurality of sections includes a proximal portion, an intermediate portion, and a distal portion, wherein the proximal portion is wider than the distal portion, and the intermediate portion tapers from a proximal end to a distal end.

15. A medical device, comprising:
an elongate member having a proximal end, a distal end, and a lumen extending therebetween, wherein the distal end defines an end face of the elongate member;
a hood, including a proximal end and a distal end, wherein a distal portion of the hood includes a plurality of sections configured to transition between a closed state and an open state, the plurality of sections defining a cavity extending distally from the end face of the elongate member; and
a sheath including a proximal end, a distal end, and a channel extending therebetween, the sheath being configured to slidably receive the hood within the channel, wherein the hood is configured to transition between the closed state while in the channel of the sheath and the open state while out of the channel, and each of the plurality of sections includes an edge, wherein when the hood is in the closed state, the edge of each of the plurality of sections is substantially parallel to a longitudinal axis of the elongate member and, when the hood is in the open state, the edges of adjacent sections are not in contact and are unconnected by material circumferentially between the edges such that a circumferential space between the edges is free of material.

16. The medical device of claim 15, wherein the plurality of sections are biased towards the open state.

17. The medical device of claim 15, further comprising a device configured to sever tissue.

18. The medical device of claim 15, wherein, when the plurality of sections are in the closed state, a distal end of the cavity is closed and distalmost ends of the plurality of sections are in contact with each other.

* * * * *